United States Patent [19]

Corvi Mora

[11] Patent Number: 4,665,224
[45] Date of Patent: May 12, 1987

[54] ESTER OF (+) 6-METHOXY-α-METHYL-2-NAPHTHALENE ACETIC ACID HAVING MUCOSECRETOLYTIC, ANTI-INFLAMMATORY, ANALGESIC, ANTIPYRETIC ACTIVITY, A PROCESS FOR ITS PREPARATION AND PHARMACEUTICAL COMPOSITIONS THEREOF

[75] Inventor: Camillo Corvi Mora, Piacenza, Italy

[73] Assignee: Camillo Corvi S.p.A., Italy

[21] Appl. No.: 734,068

[22] Filed: May 15, 1985

[30] Foreign Application Priority Data

Jun. 26, 1984 [IT] Italy ................................ 21609 A/84

[51] Int. Cl.$^4$ ............................................. C07C 69/76
[52] U.S. Cl. .................. 560/56; 260/544 B; 514/532
[58] Field of Search .......................... 560/56; 514/532

[56] References Cited

U.S. PATENT DOCUMENTS 3,904,682  9/1975  Fried et al. ............................ 560/56
4,048,330  9/1977  Fried et al. ............................ 560/56

FOREIGN PATENT DOCUMENTS 91995  10/1983  European Pat. Off. .
92031  10/1983  European Pat. Off. .

OTHER PUBLICATIONS

Corina, D. L., J. Chromatogr. 260(1), 51–62, 1983.

Primary Examiner—Paul J. Killos
Attorney, Agent, or Firm—Ostrolenk, Faber, Gerb & Soffen

[57] ABSTRACT

A novel ester of (+) 6-methoxy-α-methyl-2-naphthalene acetic acid is described.

Such ester is obtained by reaction of the (+)6-methoxy-α-methyl-2-naphthalene acetic acid chloride as prepared by a well known technique, with (−)α$^4$, α$^4$-dimethyl-1-cyclohexane-1,4-dimethanol.

There are further described pharmaceutic compositions having mucosecretolytic, anti-inflammatory analgesic and antipyretic activity, which contain the novel ester.

8 Claims, No Drawings

ESTER OF (+) 6-METHOXY-α-METHYL-2-NAPHTHALENE ACETIC ACID HAVING MUCOSECRETOLYTIC, ANTI-INFLAMMATORY, ANALGESIC, ANTIPYRETIC ACTIVITY, A PROCESS FOR ITS PREPARATION AND PHARMACEUTICAL COMPOSITIONS THEREOF

DESCRIPTION OF THE INVENTION

The subject of the present invention is an ester of (+)6-methoxy-α-methyl-2-naphthalene acetic acid with (−)α$^4$,α$^4$-dimethyl-1-cyclohexene-1,4-dimethanol, having the following formula:

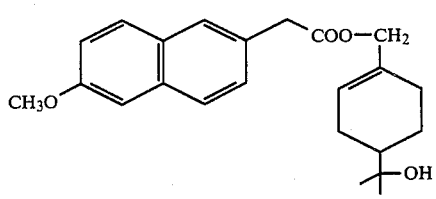

Code CO/1446    $C_{24}H_{30}O_4$ mol. wt. 382 5

(+)6-methoxy-α-methyl-naphthalene-acetoxymethyl-α,α-dimethyl-3-cyclohexene-1-methanol.

It has been found, unexpectedly, that the ester of formula (I) combines anti-inflammatory, analgesic, antipyretic activity with a marked mucolytic activity of the bronchial secretion with a very good gastric tolerability.

In the therapeutical practice, the bifunctional molecule of the present invention is suggested as a mucosecretolytic, anti-inflammatory, analgesic antipyretic drug for the treatment of bronchopneumonic respiratory diseases associated with inflammatory symptoms.

An object of the present invention is also to provide a process for the preparation of the novel bifunctional molecule, which process consists of preparing the (+)6-methoxy-α-methyl-2-naphthalene acetic acid chloride by reacting with oxalyl chloride $C_2Cl_2O_2$ (see Merck Index Xa Ed.n.6786) and thereafter condensing with (−)α$^4$,α$^4$-dimethyl-1-cyclohexene-1,4-dimethanol. The reaction is suitably carried out in an aprotic solvent, for example, an ether such as ethyl ether, tetrahydrofuran, dioxane, anhydrous methylene chloride and in the presence of an acid acceptor, preferably an organic base such as the tertiary amines of the pyridine or triethylamine type.

The reaction may be carried out within a temperature range from 10° to 100° C., preferably from 20° to 80° C.

The preparation is completed with the usual procedures of neutralization, extraction, washing and concentration to dryness and chromatography purification.

The process according to this invention will now be illustrated by the following Example, which, however, shall not limit the same.

SYNTHESIS SCHEMA OF CO/1446

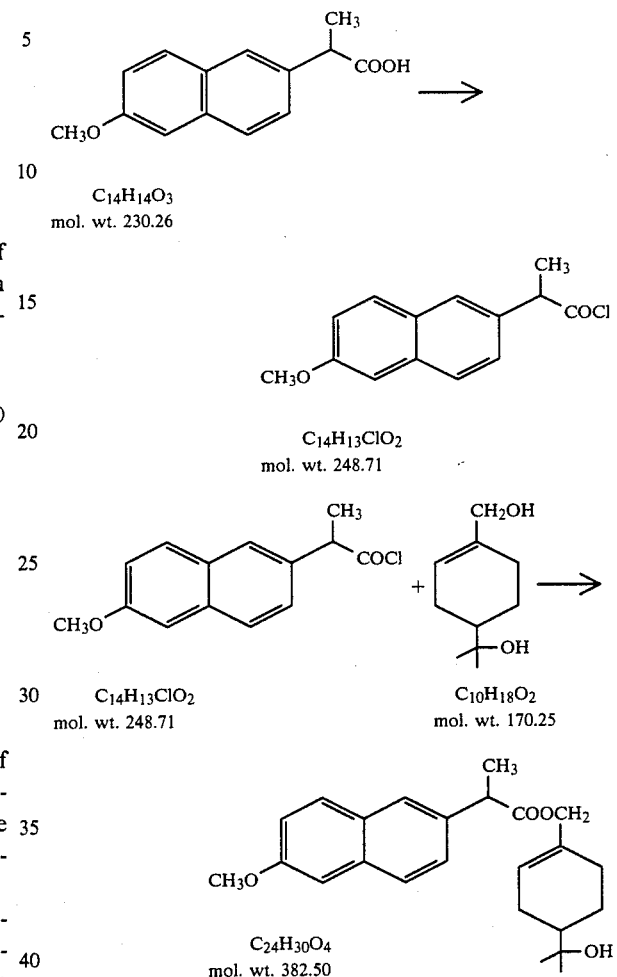

EXAMPLE

Synthesis of CO/1446

To a suspension of 17.3 g of (+)6-methoxy-α-methyl-2-napthalene acetic acid in 250 ml of methylene chloride, 20 ml of oxalyl chloride and 0.2 ml of dimethyl formamide are added. The reaction mixture is left under stirring three hours (until complete dissolution) and then it is evaporated to dryness. The acid chloride so obtained is dissolved in 50 ml of tetrahydrofuran and dropped slowly, under stirring, into a solution of 13.5 g of (−)α$^4$,α$^4$-dimethyl-1-cyclohexene-1,4-dimethanol in 50 ml pyridine. The mixture is left overnight under stirring, then poured into aqueous 20% sulphuric acid and extracted with ethyl acetate. The combined organic phases are washed with water and dried, first over anhydrous sodium sulphate and then by evaporation. The raw product (28 g) is chromatographed on silica gel by eluting with 9:1 methylene chloride-ethyl acetate. There are so obtained 24 g (85%) of a white crystalline product, m.p. 60°–63° C. CO/1446-$C_{24}H_{30}O_4$ mol. wt. 382.505

Analytical data

1. Elemental analysis

Theoretical percentages: C=75.36; H=7.91% O=16.73%. Found C=75.43%; H=7.82; C=75.41%; H=7.77; C=75.49%; H=7.84.

2. IR Spectrum

IR (solvent: CHCl$_3$; cm$^{-1}$): 3610 $\nu$ O—H; 2845 $\nu$ CH$_3$O—CH$_3$; 1728 $\nu$ C=O Ester; 1635,1608,1508 and 1483, phenyl nucleus 1266, 1177 and 855, characteristic bands.

3. NMR Spectrum

NMR (solvent: CDCl$_3$; TMS reference; δ ppm): 7.77÷7.6 and 7.5÷7.3 and 7.2÷7.03 c.a. (6H, aromatic hydrogens); 5.62 c.a (1H;=CH); 4.43 b.s. (2H;COO—CH$_2$); 3.87 s. (3H;CO$_3$—O); 3.82 q. (1H;Ar—CH) 2.2÷1.2 c.a. (7H=CH$_2$—CH—CH$_2$—); 1.57 s. (6H, gem CH$_3$).

Notes:
c.a.=complex absorption; q=quadruplet;
b.s.=broadened singlet; TMS=tetramethylsilane;
s.=singlet.

4. MS (quadrupole; direct insertion, 80 eV, 80 mA; m/z): 382 (M$^+$; 10%); 364 [(M-18)$^+$; 1%]; 230(32%); 185 (base peak); 170(15%); 155(4%); 154(9); 153(10); 152(5); 142(9); 141(16); 137(4); 135(14); 115(12); 93(25); 91(14); 79(25); 77(14); 59(92).

Analytical data of the intermediate product (CO/1430) (−)α$^4$,α$^4$-dimethyl-1-cyclohexene-1,4-dimethanol C$_{10}$H$_{18}$O$_2$ mol. wt. 170.235

IR spectrum (Nujol dispersion; cm$^{-1}$) 3270 $\nu$ OH 1290;1132;1020;925;840;811 characteristic bands.

NMR spectrum (90 MHz, CDCl$_3$ solvent; TMS reference; δppm): 5.63 centre; c.a. (1H; CH=) 3.93 b.s. (2H;CH$_2$—OH) 2.7÷1.25 c.a. (9H;CH$_2$—OH and CH$_2$—CH—CH$_2$ and (CH$_3$)$_2$COH 1.16 s. (6H; gem CH$_3$).

TMS=Tetramethylsilane
s.=singlet
b.s.=broadened singlet
c.a.=complex absorption

GC-MS (quadrupole, electronic impact, 80 eV, 70 Ma, m/z): 152 [(M-18)$^+$; 2%]; 137 [(M-18-15)$^+$; 1%]; 121 (2%); 109 (7%); 108 (4%); 94 (7.5%); 93 (7%); 91 (7.5%); 81 (8%); 79 (50%); 77 (7%); 59 base peak.

TOXICITY

Method for studying the lethal dose 50 (LD$_{50}$) in the mouse after a single administration.

Groups of 10 Swiss albine, female, adult mice (20-22 grams of body weight) fasting from the evening preceding the test, are treated orally with varying doses of the test drup suspended into hydroxyethylcellulose (0.5% w/v.)

Thereafter, the animals are fed again.

LD$_{50}$ has been calculated with the method of Litchfield J. T. and Wilcoxon F. (S. Pharmacol 96 99-113,1949) by utilizing the mortality data as obtained on the 14th day after the administration of the test drug.

TABLE 1

| TOXICITY | |
|---|---|
| Compound | LD$_{50}$ in mg/kg os. |
| CO/1446, of this invention | 4000 |
| (+)6-methoxy-α-methyl-2-naphthalene acetic acid | 885 |

The results reported in Table 1 prove a very low acute toxicity, in the mouse, of the compound of formula (I) of the present invention and a more favourable toxicity ratio of said compound (+)6-methoxy-α-methyl-2-naphthalene acetic acid.

BRONCHOSECRETAGOGUE ACTIVITY

Method of quantitative evaluation of the rabbit bronchial secretion according to Scuri R. et al. Boll. Chim. Farm. 119, 181-7; 1980.

Adult male brown rabbits (2.8-3.5 kg of body weight) to which a T shaped tracheal cannula is applied by surgical operation, as described in the above cited bibliographic reference, are used.

To the cannula, a container for periodical collection of the bronchial secretion is applied.

The study of mucoproduction, started on the fourth day after the operation, is divided into two periods (of 4 hours each), for collecting and measuring the secreted mucus. The action of the test drug is tested by administering it orally at the beginning of the second period of mucus collection and evaluating the percent increase in the mucus production (as measured gravimetrically) in the second period in comparison with the first period.

TABLE 2

| BRONCHOSECRETAGOGUE ACTIVITY | | |
|---|---|---|
| Compound | Dose in mg/kg os. | Percent increase of the bronchial mucus |
| CO/1446 | 600 | 32 |
| (+)6-methoxy-α-methyl-2-naphthalene acetic acid | 300 | 0 |

From the data as reported in Table 2, it ensues that only the compound of the present invention has bronchosecretagogue activity in the rabbit.

ANTIPHLOGISTIC ACTIVITY

Method of the carrageenin induced oedema according to Winter C. A. et al.—proc. Soc. Exp. Biol. Med—111, 544-7, 1962.

Female Wistar albine rats (120-160 grams of body weight) are utilized.

The test drug is administered orally one hour before injection of a carrageenin water suspension into the right hind paw (1%, injected volume 0.5 ml).

The volume of the injected paw is recorded simultaneously with the carrageenin injection and three hours after the same by a plethysmometer (U. Basile, mod. 7150-Comerio, Varese).

TABLE 3

| ANTIPHLOGISTIC ACTIVITY | |
|---|---|
| Compound | ED$_{50}$ in mg/kg os. |
| CO/1446 | 30 |
| (+)6-methoxy-α-methyl-2-naphthalene acetic acid | 35 |

From Table 3, it is inferred that both the compounds under examination prove to be quite active in the test of carrageenin induced oedema in the rat without any significant potency differences.

ANALGESIC ACTIVITY

Method of phenylquinone according to Hendershot L. C., J. Forsaith J. Pharmacol.—125,237, 1959.

Female Swiss albine mice (20-25 g), fasting since 2 hours are employed.

The test drug is administered orally 30 minutes before endoperitoneal injection of phenylquinone (0.08 mg/mouse).

The characteristic abdominal contractions are counted individually during a 20 minutes period.

TABLE IV

| ANALGESIC ACTIVITY | |
| --- | --- |
| Compound | ED$_{50}$ in mg/kg os. |
| CO/1446 | 3.9 |
| (+)6-methoxy-α-methyl-2-naphthalene acetic acid | 18.5 |

The data as reported in Table 4 prove that the compound of the invention is significantly more active than (+)6 methoxy-α-methyl-2-naphthalene acetic acid.

ANTIPYRETIC ACTIVITY

Method of yeast induced pyrexia in the rat.

Female Wistar albine rats, weighing 100–140 g, are employed. Animals having a rectal basal temperature from 36° to 37° C. are selected.

The testing substances are administered orally simultaneously with the pyretic agent (dry brewer's yeast suspended in water at 20% concentration, administered volume 15 ml/kg, subcutaneously) to groups of 5 animals per dose.

After 4,5,6,7 and 24 hours from the treatment, the rectal temperature of the animals is recorded by an Ellab RM6 probe, connected to an Ellab mod. TE-3 thermometer.

The activity of the drugs is evaluated by utilizing a temperature index which is given by the algebraic sum of the differences in the rectal temperature between the measured values at different times and the basal value.

TABLE 5

| ANTIPYRETIC ACTIVITY | |
| --- | --- |
| Compound | ED$_{50}$ in mg/kg os. |
| CO/1446 | 30 |
| (+)6-methoxy-α-methyl-2-naphthalene acetic acid | 14 |

The effective dose data for 50% ED$_{50}$ of the rats treated prove that the compound of the present invention has a good antipyretic activity, though lower than the control.

GASTRIC TOLERABILITY

Method of gastric ulcerogenesys by repeated drug administrations.

Fed female Wistar albine rats (140–160 g of initial body weight) are used.

The test drug is administered orally for 5 days. At the end of the experiment, the rat's stomach is withdrawn, it is dissected along the lesser curvature, washed and observed in order to disclose the presence of either gastric lesions or manifest submucosa hemorrhages.

The "ulcerogenic dose 50" (UD$_{50}$) is defined as the daily dose able to induce lesions or hemorrhages in 50% of the animals treated.

TABLE 6

| GASTRIC TOLERABILITY | |
| --- | --- |
| Compound | Ulcerogenic dose 50% (UD$_{50}$ in mg/kg os.) |
| CO/1446 | 85 |
| (+)6-methoxy-α-methyl-2-naphthalene acetic acid | 30 |

TABLE 6-continued

| GASTRIC TOLERABILITY | |
| --- | --- |
| Compound | Ulcerogenic dose 50% (UD$_{50}$ in mg/kg os.) |

The compound of the present invention is well tolerated by the gastric mucose of the rat, especially in comparison with the ED$_{50}$ values in the same species as referred for antiphlogistic and antipyretic activity.

Further, such compound is better tolerated than (+)6-methoxy-α-methyl-2-naphthalene acetic acid.

Referring to the activity performed by the compound of the invention, i.e., mucosecretolytic, anti-inflammatory, analgesic, antipyretic, activity the present invention further provides pharmaceutical compositions which contain the compound of formula (I) of the present invention in unit doses.

The therapeutical dose to be expected in the human being is of 1000—2000 mg/die as 2 administrations.

The pharmaceutical forms containing the above mentioned active ingredient are preferably those for oral and rectal administration, and particularly: capsules, tablets, syrup, granular form in sachets, and suppositories.

As excipients, there may be employed for oral pharmaceutical forms: starch, lactose, microgranular cellulose, polyvinylpyrrolidone, sorbitol and, more generally, diluting, binding, lubricating, aromatizing, flavour masking and edulcorating agents.

For the suppository form, as excipients, triglycerides of saturated fatty acids, lecithins and phospholipids, commonly used in the pharmaceutical industry, are employed.

I claim:

1. (+)6-methoxy-α-methyl-naphthalene-acetoxymethyl-α,αdimethyl-3-cyclohexene-1-methanol (I), having the formula:

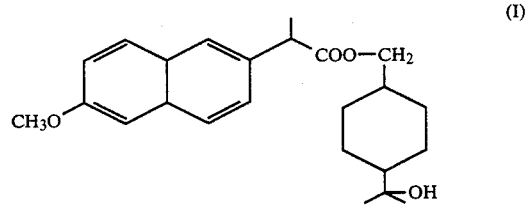

(I)

2. A process for the preparation of the compound of formula (I):

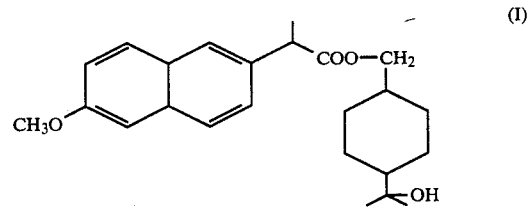

(I)

which comprises reacting (+)6-methoxy-α-methyl-2-naphthalene with oxyalyl chloride to obtain (+)6-methoxy-α-methyl-2-naphthalene acetic acid chloride and condensing the acid chloride with (−)α$^4$,α$^4$-dimethyl-1-cyclohexene-1,4-dimethanol in an aprotic solvent in the presence of an acid acceptor organic base at a temperature from 10° to 100° C.

3. The process according to claim 4, characterized in that the aprotic solvent is tetrahydrofuran.

4. The process according to claim 2, characterized in that the condensation reaction is carried out at a temperature from 10° to 20° C., in the presence of pyridine.

5. The process according to claim 4, characterized in that the aprotic solvent is dioxane.

6. The process according to claim 4, characterized in that the aprotic solvent is anhydrous methylene chloride free from ethanol.

7. Pharmaceutical compositions having mucosecretolytic, anti-inflammatory, analgesic, antipyretic activity, characterized in that they contain, as an active ingredient, the compound of formula (I) of claim 1 together with one or more pharmaceutically acceptable vahicles and/or excipients.

8. A method of imparting mucosecretolytic, anti-inflammatory, analgesic, antipyretic action in a host which comprises administrating the pharmaceutical composition of claim 7 to the host.

* * * * *